United States Patent [19]

Hüschelrath et al.

[11] Patent Number: 5,140,860

[45] Date of Patent: Aug. 25, 1992

[54] ELECTRODYNAMIC TRANSDUCER HEAD

[75] Inventors: Gerhard Hüschelrath, Laufach-Frohnhofen; Roman Koch, Hösbach, both of Fed. Rep. of Germany

[73] Assignee: Nukem GmbH, Fed. Rep. of Germany

[21] Appl. No.: 644,588

[22] Filed: Jan. 23, 1991

[30] Foreign Application Priority Data

Jan. 25, 1990 [DE] Fed. Rep. of Germany ....... 4002100

[51] Int. Cl.⁵ .............................................. G01N 29/04
[52] U.S. Cl. ........................................ 73/643; 73/644
[58] Field of Search ................. 73/643, 644; 324/226, 324/227

[56] References Cited

U.S. PATENT DOCUMENTS

| | | | |
|---|---|---|---|
| 4,449,408 | 5/1984 | Brooks et al. | 73/643 |
| 4,596,147 | 6/1986 | Behl et al. | 73/643 |
| 4,602,512 | 7/1986 | Kowol et al. | 73/643 |
| 4,665,752 | 5/1987 | Huschelrath et al. | 73/643 |

FOREIGN PATENT DOCUMENTS

| | | |
|---|---|---|
| 2845579 | 5/1979 | Fed. Rep. of Germany . |
| 3614069 | 11/1987 | Fed. Rep. of Germany . |
| 3637366 | 5/1988 | Fed. Rep. of Germany . |
| 59-228256 | 5/1986 | Japan . |
| 63-85355 | 5/1988 | Japan . |

*Primary Examiner*—Hezron E. Williams
*Assistant Examiner*—Michael J. Brock
*Attorney, Agent, or Firm*—Cushman, Darby & Cushman

[57] ABSTRACT

An electrodynamic transducer head which has at least two detachably arranged probes are allocated to one pole shoe of a magnet, and are covered by a common protective plate. The transducer head can be used for non-destructive testing of workpieces using ultrasound, for which purpose a cap of the transducer head has sliding blocks which rest on the workpiece.

13 Claims, 4 Drawing Sheets

# ELECTRODYNAMIC TRANSDUCER HEAD

BACKGROUND OF THE INVENTION

The invention relates to an electrodynamic transducer head for non-destructive testing of workpieces using ultrasound, having a magnet such as a solenoid with at least two pole shoes, to at least one of which is allocated a probe comprising an exciting and a receiving coil, said probe being covered by a protective plate on the workpiece side, with the transducer head having on the workpiece side a detachable cover such as a cap penetrated by sliding blocks resting on the workpiece.

A transducer head of this type is shown in EP-A-O 168 011. The transducer head shown in DE-C-34 01 072 is of similar design.

DE-A 36 14 069 shows a device for non-destructive testing by ultrasound, in which at least three pole pieces of changing polarity are provided, to each of which is allocated a probe. Each probe can be embedded in a separate cap, which can support a wear protection element if necessary.

The known transducer heads each have a single probe shoe or pole piece, so that a considerable quantity of apparatus is required to arrange several probes next to one another and in addition spaced apart to achieve a high measurement density. As a result, high feed rates for pipes to be checked are almost impossible to achieve to the required extent.

Even if the probe itself is protected by sliding blocks extending over it as in known measuring heads, its replacement or inspection is necessary from time to time. This requires considerable effort, since the probes are firmly installed in the transducer heads.

OBJECT OF THE INVENTION

The problem underlying present invention is to test to an adequate extent workpieces conveyed at a high feed rate, with the amount of apparatus being optimized as regards the necessary magnetic field and the number of probes to be used for the intended purpose. The possibility also had to be provided of adjusting the transducer head to the required situation without substantially altering the basic structure itself. In addition, simple inspection and if necessary replacement of a probe were to be rendered possible. Finally, it had to be ensured that the protective plate covering the probe would not necessarily be damaged or destroyed by shock-type loads.

The problem is solved in accordance with the invention in that at least two detachably arranged probes are allocated to one pole shoe of the magnet of the transducer head and are covered by a common protective plate. Accordingly, an electrodynamic transducer head is proposed in accordance with the invention that is designed with several channels to permit non-destructive testing of workpieces using ultrasound. The individual probes are arranged in a row inside the transducer head along a line, i.e. are close together, a maximum of eight probes being provided with a total length of 80 mm.

The electrodynamic transducer head in accordance with the invention permits, depending on the wall thickness and coil design, a 100% check on the wall thickness of pipes, for example, at a high feed rate. A 100% double check with, for example, an 8 mm circular disc reflector (flat-bottomed blind hole) as the reference error is possible despite an amplitude drop between the probes. The various probes operate in multiplex manner here, so that the signals of the various probes do not interfere with one another by superimposition.

Each probe comprises a magnetic field concentrator, the coils being arranged on that surface of the magnetic field concentrator facing the workpiece. This unit is preferably connected to the transducer head by plug connectors, thereby allowing the required number of probes to be fitted or replaced without problem.

The magnetic field concentrators, which comprise a material of low magnetic resistance such as silicon iron, have a rectangular cross-section which is screwed to a carrier plate. The magnetic field concentrator is penetrated by the connecting wires for the transmitting and receiving coils, the entire unit being connected by plug connectors to the transducer head as mentioned above.

The transmitting and receiving coils themselves are arranged one above the other, the transmitting coil resting directly on the magnetic field concentrator. The form of the transmitting and receiving coils can be described as pancake-shaped, i.e. disc-shaped, the receiving coil comprising resistance wire and the transmitting coil copper wire with several wires running parallel to one another. The transmitting and receiving coils are embedded here in a wear-proof sealing compound, the side facing the workpiece being ground flat.

The sensors or oscillators arranged, as already mentioned, along a straight line are protected from the workpiece by ceramic sliding blocks such that direct contact between the workpiece and the protective plate is ruled out in spite of their being passed close to the surface of the workpiece. To achieve this, the ceramic sliding blocks project above the cover, such as a cap, closing the transducer head, with preferably two ceramic sliding blocks being provided at each end of the straight on which the sensors are arranged.

The ceramic sliding blocks are low-wear, so that the entire transducer head has a long useful life. The high mechanical strength of the ceramic sliding blocks permits problem-free automatic infeed of the transducer head. Also, the ceramic sliding blocks have a low thermal conductivity, so that testing is possible at high temperatures too.

The ceramic sliding blocks can be adjusted in the direction of the workpiece being inspected to compensate for any wear. Adjustability can be achieved by intermediate pieces such as thin metal plates.

To measure any unacceptable wear on the ceramic sliding blocks, a wear protection contact is arranged between each two ceramic sliding blocks, said contact substantially comprising a spirally wound wire in a wear-proof sealing compound. The wire is lower than the free surface of the sliding block, but higher than the free surface of the preferably ceramic protective plate. The wire or wire coil is connected to a current source so that when the wire is destroyed, i.e. when the ceramic sliding blocks have become unacceptably worn, the circuit is interrupted and a warning signal thereby triggered.

The protective plate covering all the probes has a thickness preferably between 0.3 and 0.5 mm and consists, as already mentioned, of ceramic material. The protective plate is replaceably arranged inside the transducer head. For this purpose, Z-shaped holding-down means of thin metal sheet are provided that secure the longitudinal edges of the protective plate. The holding-down means are in their turn secured by the cover or cap of the transducer head. In addition, an adhesive fluid such as silicone grease is provided between the probes and the protective plate, resulting firstly in a vibration deadening effect and secondly in a deadening of the shock-type effects on the protective plate.

The magnetic field is generated via movable pole shoes over the entire length of the probes or oscillators arranged along a straight. As a result, automatic contact and lift-off is possible when the magnet yoke is fixed. Magnetization is preferably achieved by a solenoid.

BRIEF DESCRIPTION OF THE DRAWING

Further details, advantages and features of the invention are given not only in the claims and in the features to be taken from them, singly and/or in combination, but also in the following description of a preferred embodiment as shown in the drawing.

DETAILED DESCRIPTION OF A PREFERRED EMBODIMENT

Figure 1:
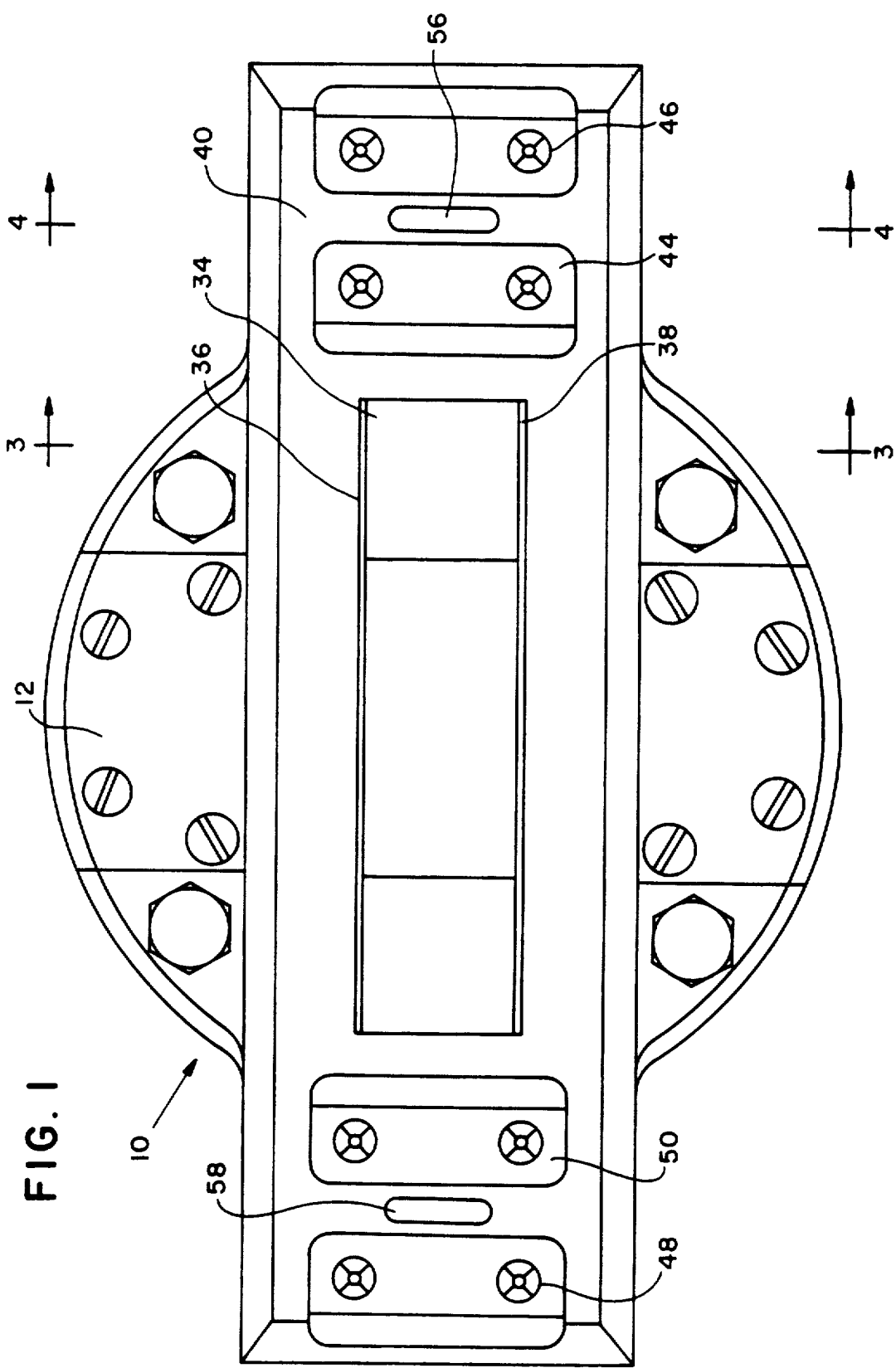
FIG. 1 shows a plan view of an electrodynamic transducer head.

FIG. 1 is a plan view of an electrodynamic transducer head (10) for non-destructive testing of a workpiece such as a pipe in a known manner using electrodynamically generated ultrasound. The magnetic field required for this purpose is generated by a solenoid, not shown, with the transducer head (10) being connected to a movable pole shoe of the solenoid.

The transducer head (10) comprises a carrier or base plate (12) connected to the pole shoe by means of connecting elements such as screws, not shown in detail.

Probes can be lined up on the base plate (12), i.e. arranged along a line, with three probes being identified with (14), (16) and (18) by way of example. Each probe (14), (16) and (18) comprises a transmitting coil (20), comprising copper wire, for example, and a receiving coil (22), which are connectable by plug contacts (24), (26) and (28) to electrical connectors, not shown in detail, for excitation of the coils or for transmission of signals received from said coils.

Figure 3:
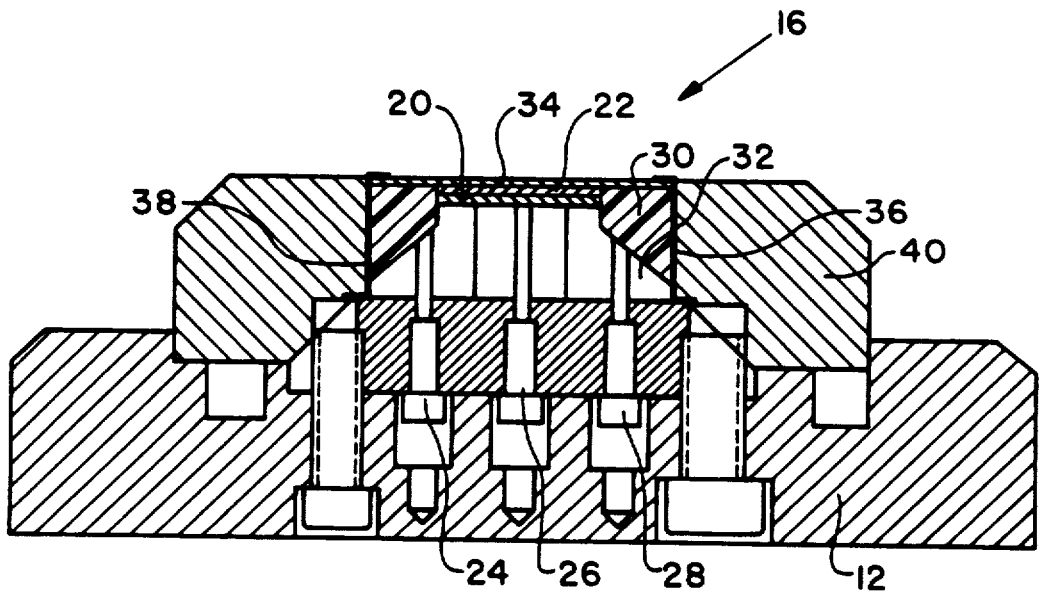
FIG. 3 shows a sectional view along the line A—A in FIG. 1.

The transmitting coil (20), which can comprise copper wire, is arranged directly on a magnetic field concentrator (32), the outline of which is indicated in FIG. 3 by a thick line. The magnetic field concentrator (32), comprising material of low magnetic resistance, has trapezoidal side surfaces as shown in FIG. 3. In the sectional view, the magnetic field concentrator (32) has a rectangular form, resulting in a kind of pyramid form with two opposite faces running parallel to one another.

The receiving coil (22), comprising resistance wire, is arranged on the workpiece side, i.e. above the transmitting coil (20). The transmitting and receiving coils (20) and (22) are embedded in a wear-proof sealing compound (30), the surface facing the workpiece being ground flat.

The compound (30) is covered by a ceramic protective plate (34) secured by Z-shaped holding means (36), (38) in the longitudinal direction. These are in turn held by a cover or cap (40) screwed to the base plate (12).

The ceramic protective plate (34) preferably extends over all the lined up probes or oscillators (14), (16), (18), thereby forming a unit. It is of course also possible to subdivide the protective plate (34) into sections.

Figure 2:
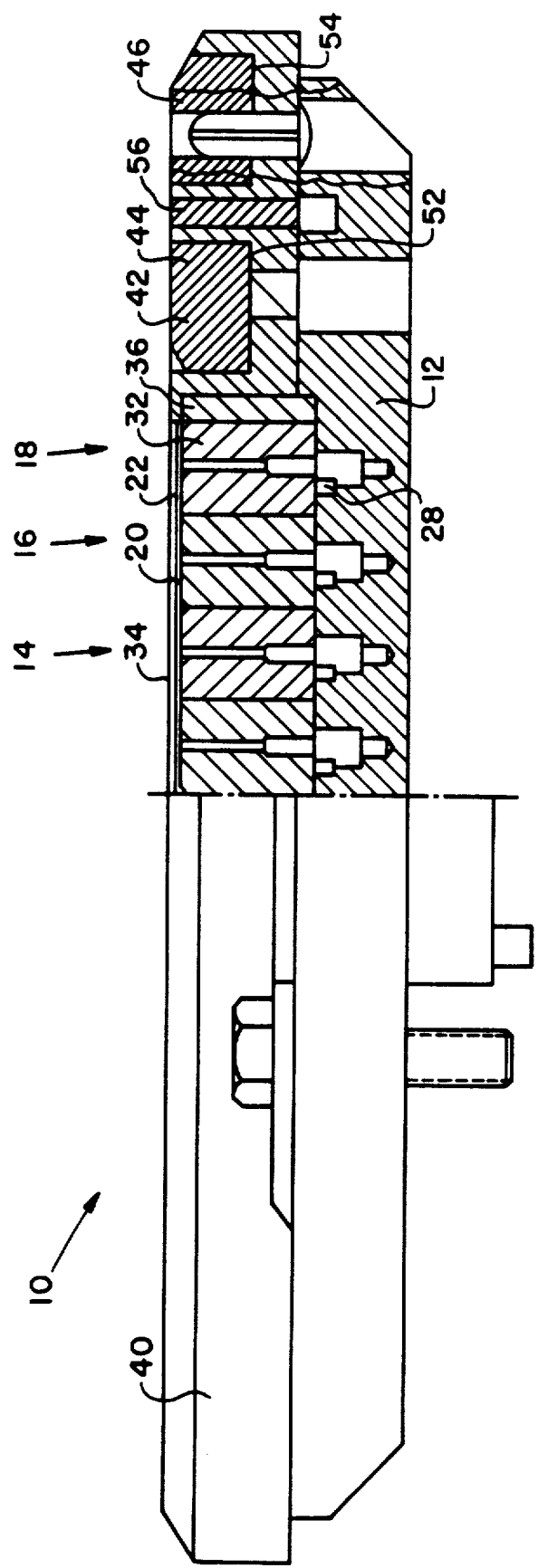
FIG. 2 shows a longitudinal section through the transducer head in accordance with FIG. 1, partially cut away.

The ceramic protective plate (34) has a thickness of between 0.3 and 0.5 mm, and is proof against abrasion and impact. In addition, there is an adhesive intermediate layer, for example of silicone, between the surface of the probe, i.e. the flat-ground sealing compound (30) and the ceramic protective plate (34), so that firstly the ceramic plate (34) is additionally held and secondly shock-type effects on the said plate are deadened. Since the probes (14), (16), (18) are connected to the transducer head (10) by plug connectors (28), the head can be provided with the required number of oscillators probes, i.e. adjusted to the respective application, without difficulty. Areas not filled in can be provided with dummy pieces. This also applies to the end areas, which in the embodiment according to FIG. 2 are filled with end blocks (36), likewise comprising a material of low magnetic resistance.

In the areas at the ends of the straight containing the probes, the cover or cap (40) is penetrated by sliding blocks (44), (46), (48), and (50). The sliding blocks (44), (46) and (48) are ceramic and have a high mechanical strength. As a result, the transducer head (10) enjoys a long useful life, since the sliding blocks (44), (46), (48) and (50) interacting with the workpiece surface are only liable to low wear. The sliding blocks (44), (46), (48), and (50) are further distinguished by low thermal conductivity, so that with the transducer head (10) in accordance with the invention tests can be conducted at high workpiece temperatures too.

The sliding blocks (44), (46), (48), (50) can be adjusted in height using intermediate pieces (52), (54) that can consist of thin metal plates. It is therefore possible to make adjustments for wear.

Figure 4:
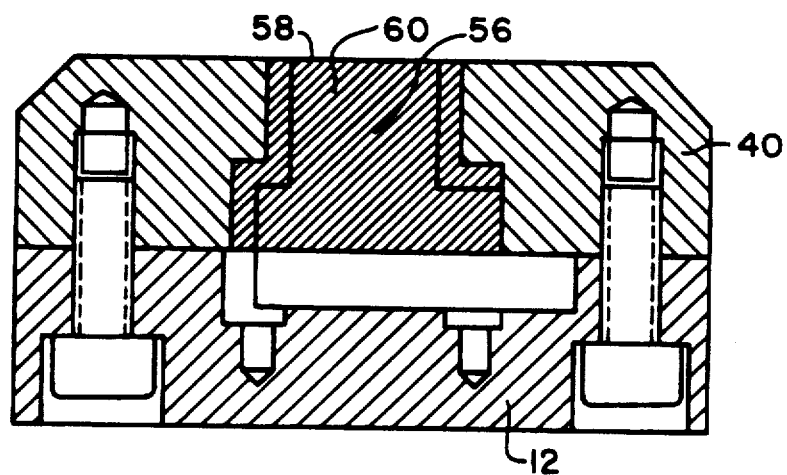
FIG. 4 shows a sectional view along the line B—B in FIG. 1.

An unacceptable wear can furthermore be detected by wear protection contacts (56), (58) arranged between the sliding blocks (44) and (46), or between (48) and (50) respectively. As FIG. 4 makes clear, each wear protection contact (56) is connected to the base plate (12) by a plug connector. The wear protection contact (56) has a spirally arranged wire (58) embedded in a sealing compound (60), the upper surface of the wire being lower than the free surface of the sliding blocks (44), (46), and (48), (50). If the sliding blocks (44), (46), and (48), (50) now become worn to an unacceptable extent, the wire (58) is destroyed by further abrasion. As a result, an alarm can be triggered if the wire (58) is arranged in a circuit.

As regards the magnetic field concentrators (32), it must be noted that the connections for the transmitting and receiving coils (20) and (22) pass through them, as can be seen in FIG. 3. The concentrator (32) preferably comprises silicon-iron for eddy-current damping and for prevention of sound in the pole shoe and for damping of the coils (short pulse for wall thickness measurement). In addition, the concentrators (32) can be slotted to achieve the same effects.

The transducer head (10) is preferably connected to a movable pole shoe, thereby permitting automatic contact and lift-off when the magnet yoke is fixed. The magnetic field itself is preferably generated with a solenoid.

Figure 5:
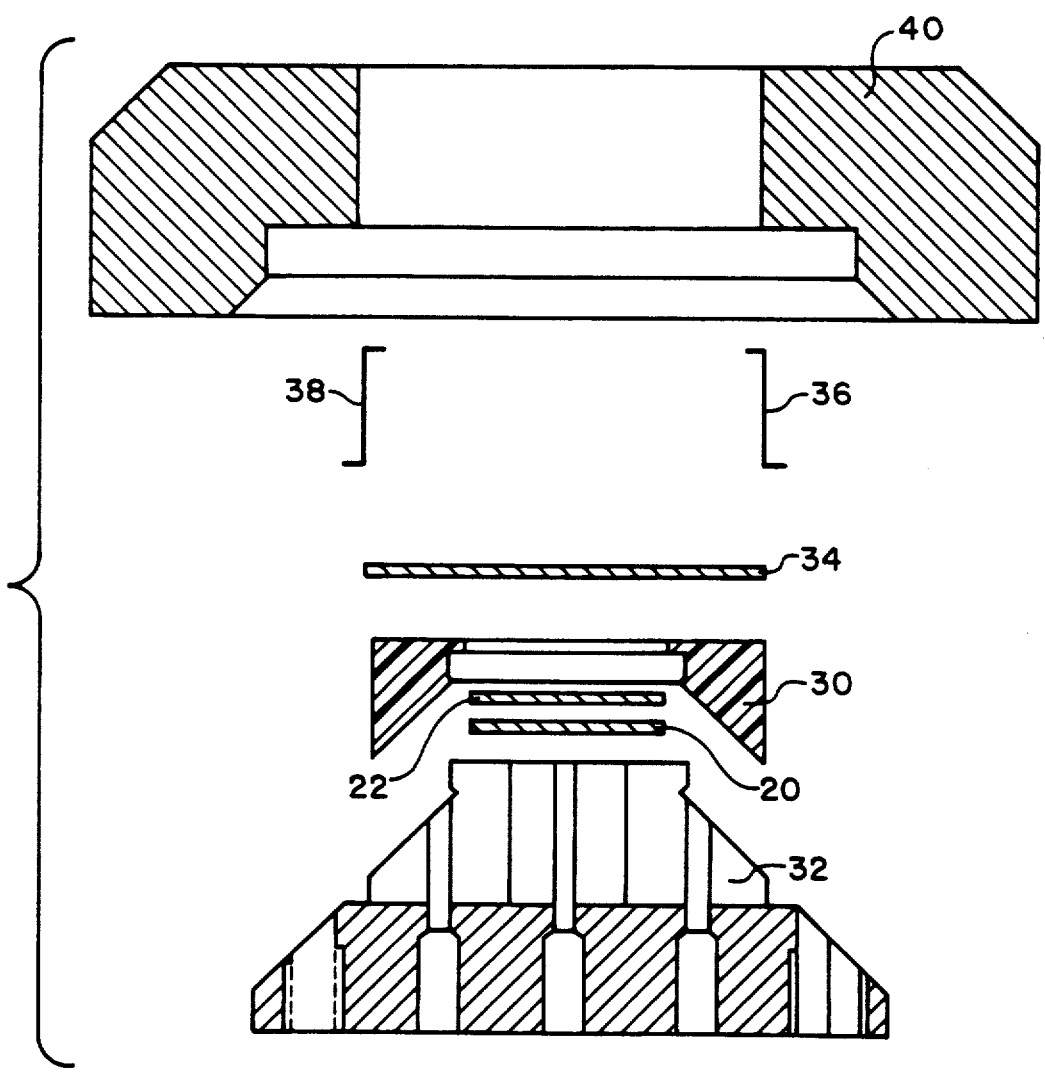
FIG. 5 shows an exploded view of substantial elements of the transducer head.

The substantial components of a probe with magnetic field concentrator (32), transmitting and receiving coils (20) and (22), the sealing compound (30) holding the latter, the ceramic protective plate (34), the Z-shaped holding means (36) and (38) holding said plate, and the cover (40), are shown again in an exploded view in FIG. 5.

We claim:

1. An electrodynamic transducer head for nondestructive testing of workpieces using ultrasound, having a magnet such as a solenoid with at least two pole shoes, to at least one of which is allocated a probe comprising an exciting and a receiving coil, said probe being covered by protective plate on a workpiece side, which is a side closer to the workpiece, with said transducer head having on the workpiece side a detachable cover, which is penetrated by sliding blocks resting on said workpiece, characterized in that at least two detachably arranged probes are allocated to one pole shoe of said magnet of said transducer head and are covered by a common protective plate.

2. A transducer head according to claim 1, characterized in that the probes are arrangeable close together in a row and are of identical design.

3. A transducer head according to claim 1, characterized in that each probe comprises a magnetic field concentrator fastened together with said probe as a unit in said transducer head.

4. A transducer head according to claim 3, characterized in that the unit is fastened to said electrodynamic transducer head by plug connectors.

5. A transducer head according to claim 1, characterized in that the probes are arranged along a straight line, in that at least two sliding blocks spaced apart and extending at least over sections of the cap surface are arranged at the each end of said straight line, and in that a wear protection element is provided between each two sliding blocks.

6. A transducer head according to claim 5, characterized in that the sliding blocks are designed to be adjustable in the direction of the workpiece by means of intermediate pieces including thin metal plates.

7. A transducer head according to claim 1, characterized in that the protective plate is secured by Z-shaped curved holding means which are in turn held by the cap (40) of said transducer head.

8. A transducer head according to claim 1, characterized in that an adhesive fluid including silicone grease is provided between the probe surface facing the workpiece and the protective plate.

9. A transducer head according to claim 1, characterized in that the transmitting and receiving coils are embedded in a wear-proof sealing compound which is ground flat on the workpiece side.

10. A transducer head according to claim 9, characterized in that the transmitting and receiving coils are arranged one above the other in disc form, said transmitting coil being arranged directly on the magnetic field concentrator.

11. A transducer head according to claim 3, characterized in that the magnetic field concentrator has a rectangular cross-section with trapezoidal side faces running parallel to one another.

12. A transducer head according to claim 11, characterized in that the magnetic field concentrator consists of silicon iron.

13. A transducer head according to claim 11, characterized in that the magnetic field concentrator is slotted.

* * * * *